US00PP37656P2

(12) United States Plant Patent
Hong et al.

(10) Patent No.: US PP37,656 P2
(45) Date of Patent: Sep. 1, 2026

(54) ***ILEX* PLANT NAMED 'HARVEST'**

(50) Latin Name: ***Ilex dabieshanensis* x *latifolia***
Varietal Denomination: HARVEST

(71) Applicant: Institute of Botany, Jiangsu Province and Chinese Academy of Sciences, Nanjing (CN)

(72) Inventors: Chen Hong, Nanjing (CN); Zhou Ting, Nanjing (CN); Chong Xinran, Nanjing (CN); Lu Bo, Nanjing (CN); Li Naiwei, Nanjing (CN); Zhou Yanwei, Nanjing (CN); Cai Xiaolong, Nanjing (CN); Lu Xiaoqing, Nanjing (CN); Wang Chuanyong, Nanjing (CN)

(73) Assignee: Institute of Botany, Jiangsu Province and Chinese Academy of Science (CN)

( * ) Notice: Subject to any disclaimer, the term of this patent is extended or adjusted under 35 U.S.C. 154(b) by 0 days.

(21) Appl. No.: 19/325,093

(22) Filed: Sep. 10, 2025

(51) Int. Cl.
*A01H 5/08* (2018.01)
*A01H 6/00* (2018.01)

(52) U.S. Cl.
USPC ..... Plt./247

(58) Field of Classification Search
USPC ..... Plt./247
CPC ... A01H 5/08; A01H 5/12; A01H 5/00; A01H 6/00
See application file for complete search history.

(56) References Cited

PUBLICATIONS

Zhou et al Ning Qing 1: A New Holly Cultivar With Broadly Ovate Leaf Morphology, HortScience 58(12): 1626-1627, 2023. (Year: 2023).*

* cited by examiner

*Primary Examiner* — June Hwu

(57) ABSTRACT

A new and distinct cultivar of *Ilex* plant named 'HARVEST' is disclosed characterized by dense fruit set at lateral axils. Fruits are distinctively incised with a residual calyx. Young foliage is uniquely colored Yellow-Green 154B. The new variety is useful as an ornamental plant.

3 Drawing Sheets

Latin name of the genus and species: *Ilex dabieshanensis* x *latifolia*.

Variety denomination: 'HARVEST'.

BACKGROUND OF THE INVENTION

The new cultivar, hereinafter referred to as 'HARVEST', was discovered as a planned breeding program conducted in Nanjing, China. The seed parent is an unnamed, unpatented *Ilex dabieshanensis* K. Yao & M. B. Deng. The pollen parent is an unnamed, unpatented *Ilex latifolia* Thunb. The crossing resulting in the new cultivar 'Harvest' was made during April of 2014 at a botanic garden in Nanjing, China. The inventors selected the new variety at the same botanic garden in Nanjing, China in the October of 2018.

First asexual propagation of 'HARVEST' by semi-softwood cuttings was made at the same botanic garden in July of 2019. The inventors continued controlled testing and propagation, assessing stability of the unique characteristics of this variety. At least four generations have been reproduced and have shown that the unique features of this cultivar are stable and reproduced true to type.

SUMMARY OF THE INVENTION

The cultivar 'HARVEST' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'HARVEST'. These characteristics in combination distinguish 'HARVEST' as a new and distinct *Ilex* cultivar:

1. Dense fruit set at lateral axils.
2. Distinctive incised fruits with residual calyx.
3. Unique Yellow-Green 154B color of young foliage.

COMPARISON TO PARENT VARIETIES

*Ilex* 'HARVEST' differs from the seed parent in the following:

1. Young foliage color of 'Harvest' is Yellow-Green 154B; young foliage color of the seed parent is Yellow-Green 144A.
2. Fruits of 'Harvest' are distinctively incised with a residual calyx. Fruits of the seed parent lack incision and a residual calyx.

*Ilex* 'HARVEST' differs from the pollen parent in the following:

1. Foliage of 'Harvest' is thicker and more leathery than foliage of the pollen parent.
2. Foliage shape of 'Harvest' is elliptic; foliage shape of the pollen parent is oblong.
3. Foliage length of 'Harvest' is 9.0 to 9.5; foliage length of the pollen parent varies from 8 to 19 cm.

COMMERCIAL COMPARISON

*Ilex* 'HARVEST' can be compared to the commercial variety *Ilex* 'Zi Lin', unpatented. Plants are similar in most horticultural characteristics, including upright plant habit and a distinct new stem coloration; however, plants of the new variety differ in the following:

1. Young foliage color of 'Harvest' is Yellow-Green 154B; young foliage color of 'Zi Lin' is Yellow-Green 144C.
2. Foliage shape of 'Harvest' is elliptic; foliage shape of this comparator is broad elliptic.
3. Fruits of 'Harvest' are distinctively incised with a residual calyx. Fruits of 'Zi Lin' are umbilicate and lack incision.

BRIEF DESCRIPTION OF THE PHOTOGRAPHS

The accompanying photographs illustrate in full color a typical plant of 'HARVEST' grown outdoors in the ground in Nanjing, China.

Figure 1:
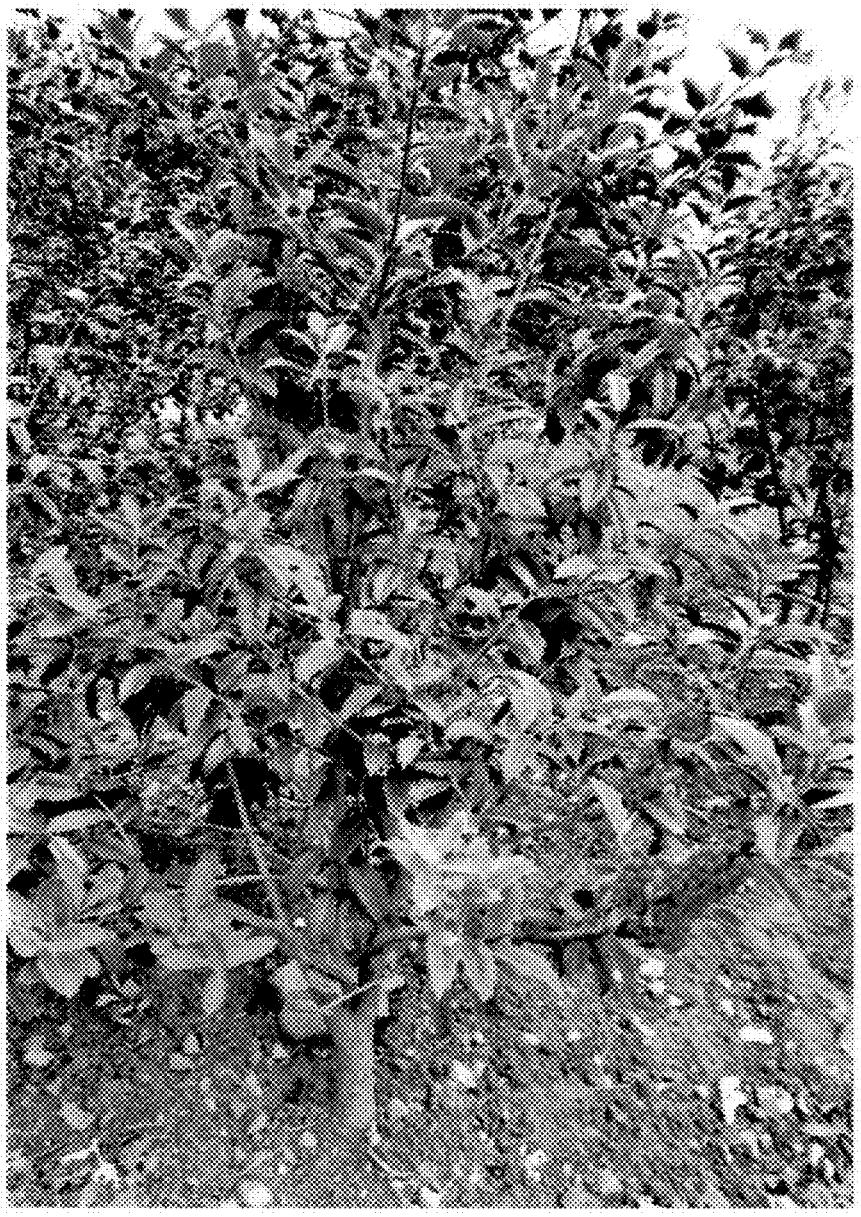
FIG. 1 is a fruiting plant of approximately 7 years old.
Figure 2:
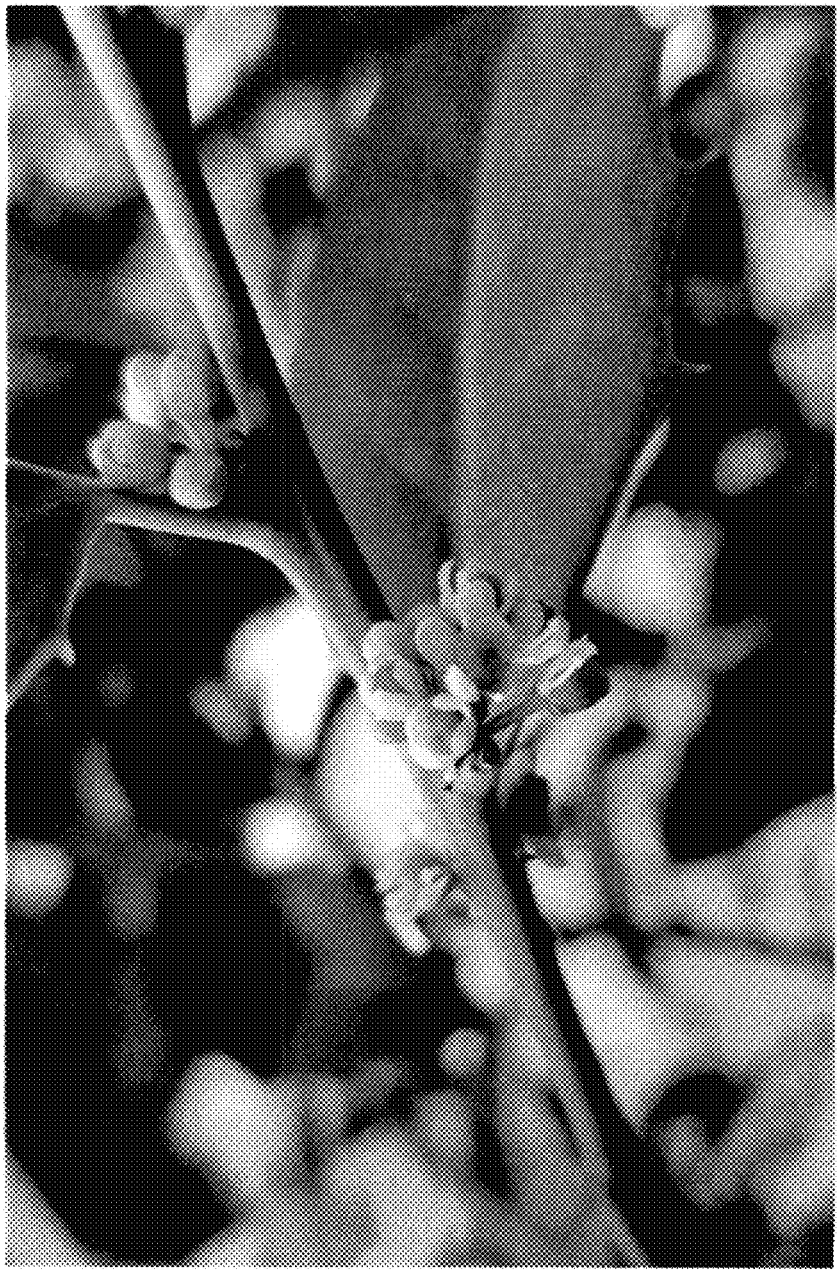
FIG. 2 is a close-up view of flowers and foliage from the same plant.
Figure 3:
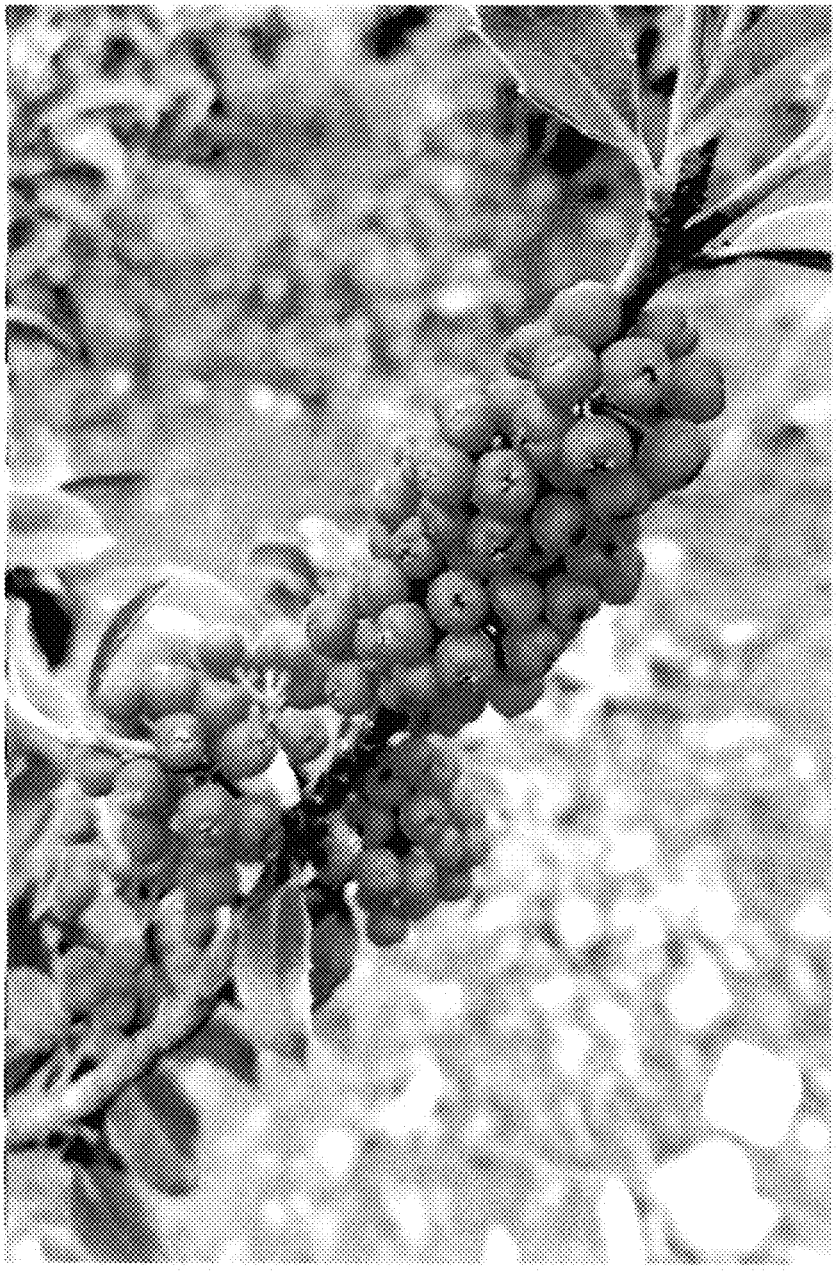
FIG. 3 is a close-up view of a fruiting branch.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'HARVEST' plants grown outdoors in Nanjing, China. Temperatures ranged from about 0° C. to 40° C. during the day and −5° C. to 30° C. at night. Plants are approximately 9 years old, and planted in the ground. Measurements and numerical values represent averages of typical plant types.

Botanical classification: *Ilex dabieshanensis* x *latifolia* 'HARVEST'.

PROPAGATION

Typically by semi-hardwood cuttings in Spring and Summer.

Root description: Semi-woody, moderately dense roots. Colored near RHS Grey-Brown 199A.

PLANT

Growth habit: Ovoid crown. Semi-open (dense).

Height: Approximately 185 cm.

Plant spread: Approximately 65 cm.

Branching characteristics: 3 primary branches each with 3 secondary lateral branches. No pinching required for lateral branch formation.

Lateral branches:

*Length*.—Average range 60 cm to 80 cm.
*Diameter*.—10 to 13 mm.
*Internode length*.—13 to 25 mm.
*Shape*.—Round and ridged.
*Aspect*.—Straight, 30° to 45° from center.
*Texture*.—Glabrous.
*Strength*.—Very strong, resists breakage, non-brittle.
*New growth color*.—Green 143C.
*Mature color*.—Yellow-Green 148A.

Other: Lenticels not observed. Oldest basal stem is colored near Greyed-Brown 199A.

FOLIAGE

Leaf:

*Arrangement*.—Single, alternate whorled.
*Density*.—Moderately dense.
*Average length*.—Approximately 9 to 9.5 cm.
*Average width*.—Approximately 3.5 to 4.0 cm.
*Shape of blade*.—Elliptic.
*Apex*.—Acute.
*Base*.—Cuneate.
*Attachment*.—Stalked.
*Margin*.—Finely serrate. 5 (most commonly) to 7 spines one each side of the leaf (total 10 to 14). Spines are slightly sharp and colored near Yellow-Green 144C.
*Aspect*.—Flat to very slightly reflexed.
*Texture of top surface*.—Glabrous.
*Texture of bottom surface*.—Glabrous.
*Appearance of top surface*.—Leathery.
*Appearance of bottom surface*.—Matte.
*Color*.—Young foliage upper side: Yellow-Green 154B. Young foliage under side: Yellow-Green 144C. Mature foliage upper side: Yellow-Green 147A. Mature foliage under side: Yellow-Green 146B.
*Venation*.—Type: Pinnate. Venation color upper side: Yellow-Green 146C. Venation color under side: Yellow-Green 146C.

Petiole:

*Average length*.—Approximately 12 to 14 mm.
*Diameter*.—Approximately 2 mm.
*Color*.—Yellow-Green 144C upper and lower surfaces.

FLOWER

Axillary flowers, mostly occurring at stem terminus. Flowering begins around mid-April in Nanjing, China. Typically flowering around 4 weeks. Individual flowers last about 5 to 7 days. Self-cleaning.

Flower size:

*Diameter*.—9 to 11 mm.
*Depth*.—5 to 7 mm.

Petals:

*Petal arrangement*.—Cruciform.
*Length*.—3 to 5 mm.
*Width*.—2 to 3 mm.
*Shape*.—Obovate.
*Margin*.—Entire.
*Apex*.—Obutuse.
*Base*.—Broad cuneate.
*Petal quantity*.—4.
*Texture*.—Glabrous all surfaces.
*Appearance*.—Matte all surfaces.
*Color*.—When opening: Upper surface: Yellow-Green 151A. Lower surface: Yellow-Green 151A. Fully opened: Upper surface: Yellow-Green 151A. Lower surface: Yellow-Green 151A.

Bud:

*Shape*.—Ellipsoid.
*Length*.—Approximately 5 to 7 mm.
*Diameter*.—Approximately 3 mm.
*Color*.—Yellow-Green 151A.

Sepals:
*Quantity.*—4.
*Length.*—0.5 mm.
*Width.*—0.3 mm.
*Shape.*—Deltate.
*Color.*—Interior Surface: Yellow-Green 151A. Exterior Surface: Yellow-Green 151A.
*Texture.*—All surfaces glabrous.
Fragrance: None detected.
Peduncle:
*Length.*—3.5 to 5 mm.
*Diameter.*—1 mm.
*Color.*—Yellow-Green 149A.
*Texture.*—Glabrous.
*Strength.*—Moderate.
*Angle.*—30° to 45° from attachment.

REPRODUCTIVE ORGANS

Gynoecium:
Pistil:
*Number.*—1 per flower.
*Length.*—3.7 to 4.7 mm.
*Style length.*—3.3 to 3.7 mm.
*Stigma shape.*—Linear.
*Stigma color.*—Yellow-Green 151C.
*Ovary shape.*—Round.
*Ovary color.*—Yellow-Green 151C.
Androecium:
Stamens: Degenerate or sterile.
*Number.*—4 per flower.
*Filament length.*—2 to 3 mm.
*Anther shape.*—Linear.
*Anther color.*—Yellow-Green 150D.
*Pollen.*—Not observed due to stamen degeneration or sterility.

FRUIT AND SEED

Self-fertile: No.
Pollinator: *Ilex latifolia* is the observed male pollinator.
Fruit:
*Type.*—Simple indehiscent berry.
*Arrangement.*—Densely fruiting at lateral axils.
*Shape.*—Globose. Incised.
*Length.*—8 to 9 mm.
*Width.*—10 to 12 mm.
*Base.*—Residual calyx present.
*Color.*—RHS Red 43A.
*Texture.*—Glabrous.
*Quantity.*—Axillary clusters have an average range of 50 to 70 fruits.
Seed: Seed production has not been observed.

OTHER CHARACTERISTICS

Disease and pest resistance: Neither resistance nor susceptibility to normal diseases and pests of *Ilex* observed.
Temperature tolerance: Observed cold tolerant to −8° C. Observed heat tolerant to 40° C.

What is claimed is:

1. A new and distinct cultivar of *Ilex* plant named 'HARVEST' as herein illustrated and described.

* * * * *